United States Patent
Wong et al.

(10) Patent No.: US 6,346,517 B1
(45) Date of Patent: Feb. 12, 2002

(54) SYNERGY BETWEEN LOW MOLECULAR WEIGHT HEPARIN AND PLATELET AGGREGATION INHIBITORS, PROVIDING A COMBINATION THERAPY FOR THE PREVENTION AND TREATMENT OF VARIOUS THROMBOEMBOLIC DISORDERS

(75) Inventors: Pancras C. Wong, Wilmington, DE (US); Shaker A. Mousa, Lincoln University, PA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/523,395

(22) Filed: Mar. 10, 2000

Related U.S. Application Data (60) Provisional application No. 60/123,820, filed on Mar. 11, 1999.

(51) Int. Cl.[7] ........................ A61K 31/725; A61K 31/42
(52) U.S. Cl. .................... 514/56; 514/378; 514/380
(58) Field of Search .......................... 514/56, 380, 378

(56) References Cited

FOREIGN PATENT DOCUMENTS

| EP | 0735050 A | 10/1992 |
| WO | 9514683 A | 6/1995 |
| WO | 9735615 A | 10/1997 |
| WO | 9938827 A | 8/1999 |

OTHER PUBLICATIONS

Coller, B. S. 1997, FAB. Thromb. Haemost., GPIIb/IIIa Antagonists: Pathophysiologic and Therapeutic Insights from Studies of C7E3, 78, 1, 730–735.
White, H. D. 1997, Am. J. Cardiol., Unmet Therapeutic Needs in the Management of Acute Ixchemia, 80, 4A, 2B–10B.
Tcheng, J. E., 1996, Am. J. Cardiol., Glycoprotein IIb/IIIa Receptor Inhibitors: Putting EPIC, IMPACT II, RESTORE, and EPILOG Trials Into Perspective, 78, 3A, 35–40.
Schafer A.I. Jan. 15, 1997, Hospital Practice, Low molecular–weight heparin for venous thromboembolism, 99–106.
Montalescot G. et al., "Low molecular weight heparins in the cardia catheterization laboratory.", J. Thromb. Thrombolysis, (Jun. 1999) 7 (3) 319–23, ref: 27, XP000933777, p. 321–322, table 2.
P. Theroux, "Antithrombotic treatment of acute coronary syndromes", Canadian Journal Of Cardiology, vol. 14, No. se, Aug. 1, 1998, pp. 6e–10e, XP000934137, p. 6E, table 4.
Yaryura R. et al., "Low–molecular–weight heparin and abciximab for thrombo–occlusive saphenous vein graft disease. Report of 2 cases.", Texas Heart Institute Journal, vol. 24, No. 4, 1997, pp. 379–383, XP000934140, p. 380, p. 382, right–hand column.
Simonneau et al., "A comparison of low–molecular–weight heparin with unfractionated heparin for acute pulmonary embolism", New England Journal Of Medicine, vol. 337, No. 10, Sep. 4, 1997, pp. 663–669, XP000934147, p. 668.
Habis M. et al., "[Antithrombotic agents in unstable angina. Review of clinical trials]. Les antithrombotiques de l'angor instable. Bilan des essais cliniques." Annales De Cardiologie et D Angeiologie, (Jan. 1998), 47 (1) 21–31., XP000933774, the whole document.
Siragusa et al., "Low–molecular–weight heparins and unfractionated heparin in the treatment of patients with acute venous thromboembolism: Results of a meta–analysis", American Journal of Medicine, vol. 100, Mar. 1996, pp. 269–277, XP000934175, the whole document.
Simpson et al., "Long–term use of the low molecular weight heparin tinzaparin in haemodialysis", Haemostasis, vol. 26, Apr. 1, 1996, pp. 90–97, XP000934173, p. 92, left–hand column, paragraph 4.

*Primary Examiner*—Raymond Henley, III
(74) *Attorney, Agent, or Firm*—Robert W. Black; Rosemarie Wilk-Orescan; Kalim S. Fuzail (57) ABSTRACT

This invention is directed to a combination therapy comprising the administration of a low molecular weight heparin such as tinzaparin and a platelet GPIIb/IIIa antagonist such as roxifiban for treating, preventing and reducing the risk of thromboembolic disorders.

16 Claims, 5 Drawing Sheets

Effect of Roxifiban on the Antiplatelet Efficacy of Tinzaparin in Thrombin Induced Human Platelet Aggregation

Figure 1

Synergistic Antiplatelet Effects of Tinzaparin and Roxifiban on Thrombin Induced Platelet Aggregation Subtherapeutic doses of tinzaparin and roxifiban in combination exerted a distinct synergy in blocking platelet aggregation as well as clot formation mediated by TF, Xa, or thrombin

SYNERGY BETWEEN LOW MOLECULAR WEIGHT HEPARIN AND PLATELET AGGREGATION INHIBITORS, PROVIDING A COMBINATION THERAPY FOR THE PREVENTION AND TREATMENT OF VARIOUS THROMBOEMBOLIC DISORDERS

CROSS-REFERENCE TO RELATED APPLICATIONS

This application claims the benefit of U.S. Provisional Application No. 60/123,820, filed Mar. 11, 1999.

FIELD OF THE INVENTION

This invention is directed to a combination therapy comprising the administration of a low molecular weight heparin such as tinzaparin and a platelet GPIIb/IIIa antagonist such as roxifiban for treating, preventing and reducing the risk of thromboembolic disorders.

BACKGROUND OF THE INVENTION

Thromboembolic diseases, including stable and unstable angina pectoris, myocardial infarction, stroke and lung embolism, are the major cause of disability and mortality in most developed countries. Platelet glycoprotein IIb/IIIa (GPIIb/IIIa) is the main platelet receptor for fibrinogen and other adhesive glycoproteins, including fibronectin, vitronectin and von Willebrand factor. Interference of ligand binding with this receptor has been proven beneficial in animal models of thromboembolic disease (Coller, B. S. GPIIb/IIIa Antagonists: Pathophysiologic and Therapeutic Insights from Studies of C7E3 FAB. Thromb. Haemost. 78: 1, 730–735, 1997), and in limited studies involving human subjects (White, H. D. Unmet Therapeutic Needs in the Management of Acute Ixchemia. Am. J. Cardiol. 80: 4A, 2B-10B, 1997; Tcheng, J. E. Glycoprotein IIb/IIIa Receptor Inhibitors: Putting EPIC, IMPACT II, RESTORE, and EPI-LOG Trials Into Perspective. Am. J. Cardiol. 78: 3A, 35–40, 1996).

The integrin GPIIb/IIIa, also referred to as the platelet fibrinogen receptor, is the membrane protein mediating platelet aggregation. GPIIb/IIIa in activated platelets is known to bind four soluble RGD containing adhesive proteins, namely fibrinogen, von Willebrand factor, fibronectin, and vitronectin. The term "RGD" refers to the amino acid sequence Arg-Gly-Asp. The binding of fibrinogen and von Willebrand factor to GPIIb/IIIa causes platelets to aggregate. GPIIb/IIIa antagonists represent an important new approach for anti-platelet therapy for the treatment of thromboembolic disorders.

Platelet activation and aggregation are involved in unstable angina and acute myocardial infarction, in reocclusion following thrombolytic therapy and angioplasty, in transient ischemic attacks and in a variety of other vaso-occlusive disorders. When a blood vessel is damaged either by acute intervention such as angioplasty, or more chronically by the pathophysiological processes of atherosclerosis, platelets are activated and adhere to the disrupted surface and to each other. This activation, adherence and aggregation may lead to occlusive thrombus formation in the lumen of the blood vessel. Since the binding of fibrinogen to an activated membrane-bound glycoprotein complex (GPIIb/IIIa) is an obligatory component of normal aggregation, GPIIb/IIIa is an attractive target for an antithrombotic agent.

Antiplatelet therapy has been used in a wide variety of cardiovascular disease states and in conjunction with interventional therapy such as coronary artery or peripheral bypass grafting, cardiac valve replacement, and percutaneous transluminal coronary angioplasty (PTCA). Available drugs, such as aspirin and ticlopidine (TICLID®), have shown efficacy in syndromes involving vascular occlusion, presumably due to sustained inhibition of platelet function. However, the inhibitory effects of aspirin and ticlopidine are dependent upon the agonist, which activates the platelet. For example, aspirin is effective in blocking platelet aggregation induced by agonists such as collagen that are dependent upon the cyclooxygenase pathway. It is however, less effective against concentrations of thrombin which can act by cyclooxygenase independent pathways. Likewise, the inhibitory effects of tidopidine, which inhibits ADP induced platelet aggregation, can be overcome by combinations of agonists.

The effect of heparin on blood coagulation is exploited clinically as an anticoagulant and antithrombotic drug. Heparin belongs to the group of polysaccharides known as glycosaminoglycans (GAGs), and is composed of alternating 1–4-linked hexuronic acid and D-glucosamine. Both the hexauronic acid and the glucosamine residues are sulfated in a complex pattern resulting in extensive structural variability. Because of its high negative-charge density, heparin is able to interact with clusters of basic amino acids on numerous proteins and cell membranes, such as coagulation proteinases, serine protease inhibitors, growth factors, lipoprotein and hepatic lipase, apolipoproteins B and E, adhesive matrix proteins, platelets, and endothelial cells.

Low molecular weight heparins (LMWHs), obtained from standard unfractionated heparin (UFH), are as effective as standard unfractionated heparin for prophylaxis and treatment of venous thromboembolism and have fewer side effects (Schafer A. I. Low molecular-weight heparin for venous thromboembolism. Hospital Practice, Jan. 15, 1997, pp. 99–106). The current available low molecular weight heparins include, for example, tinzaparin, certoparin, parnaparin, nadroparin, ardeparin, enoxaparin, reviparin and dalteparin (fragmin).

A combination therapy comprising the administration of a GPIIb/IIIa antagonist with either aspirin or a low molecular weight heparin is useful in the treatment of thrombotic disorders including atherosclerotic arterial disease, valvular heart disease, cerebrovascular disease such as stroke, atrial fibrillation, coronary artery disease such as myocardial infarction and unstable angina, coronary artery bypass grafts, peripheral vascular disease, thromboembolic complications of prosthetic cardiovascular devices such heart valves and vascular grafts. These combinations are also expected to be useful when coupled with endovascular stenting procedures, such as percutaneous transluminal coronary angioplasty, to prevent subsequent arterial thrombus formation and reocclusion.

A number of criteria must be considered when contemplating a combination therapy: (a) each agent demonstrates significant clinical benefits in various thromboembolic disorders; (b) both agents act at different mechanistic levels and with different capacities; (c) combination of the agents at adjusted doses could improve efficacy and/or safety. In that regard, a wealth of clinical experience exists, especially for UFH and intravenous platelet GPIIb/IIIa antagonists in acute coronary syndromes (ACS). The potential clinical benefit of the platelet GPIIb/IIIa antagonist abciximab in ACS was demonstrated in the pivotal "Evaluation of c7E3 Fab in the Prevention of Ischemic Complications" (EPIC) and "Evaluation in Percutaneous transluminal coronary angioplasty to Improve Long-term Outcome with abciximab GPIIb/IIIa blockade" (EPILOG) trials. In the EPIC trial, there was significant excess bleeding that occurred when UFH was used in its full dose with abciximab leading to the EPILOG trial, where a reduced dose of UFH was used. The lower UFH dosage led to an improved safety profile without compromising the efficacy observed in the EPIC trial. Similarly, the "Platelet Receptor Inhibition in Ischemic Syndrome Management" (PRISM) and the "PRISM in Patients Limited by Unstable Signs and Symptoms" (PRISM-PLUS) trials evaluated whether administration of aspirin (PRISM) or UFH plus tirofiban (PRISM-PLUS) would improve clinical outcomes in the management of unstable angina. The control group in PRISM-PLUS received intravenous UFH only. Tirofiban plus UFH was significantly more effective than UFH alone in reducing the incidence of death, myocardial infarction, or refractory ischemia within 7 days after randomization. This finding suggested improved efficacy following administration of the combination of UFH and a GPIIb/IIIa antagonist. Other trials of GPIIb/IIIa antagonists with adjusted-dose UFH are currently under investigation. The advantages of LMWHs over UFH are significant (as described hereinafter), therefore the combination of a LMWH with a platelet GPIIb/IIIa receptor antagonist has great potential benefits when combined at the right dose regimens.

SUMMARY OF THE INVENTION

One object of the present invention is to provide a method of treating thrombosis in a mammal comprising: administering to said mammal the combination in a therapeutically effective amount of (i) a GPIIb/IIIa antagonist selected from the group consisting of abciximab, eptifibatide, tirofiban, amifiban, lefradafiban, sibrafiban, orbofiban, xemilofiban, a compound of the formula (A):

and a compound of the formula (B) (roxifiban):

and (ii) aspirin, or the GPIIb/IIIa antagonist (i) and (iii) a low molecular weight heparin selected from the group consisting of tinzaparin, certoparin, parnaparin, nadroparin, ardeparin, enoxaparin, reviparin and dalteparin, wherein at least one of the antagonist and aspirin, or at least one of the antagonist and the low molecular weight heparin, is administered in a subtherapeutic amount.

Another object of the present invention is to provide a method of treating thrombosis in a mammal wherein the combination of (i) and (ii) or (iii) above are administered in amounts to provide a synergistic effect.

Another object of the present invention is to provide a method of treating thrombosis in a mammal by administering to said mammal the combination in a therapeutically effective amount of tissue plasminogen activator ("TPA"), and a GPIIb/IIIa antagonist compound of the formula wherein at least one of said agents is administered in a subtherapeutic dose.

Another object of the present invention is to provide a method for treating a condition selected from the group: acute coronary ischemic syndrome, thrombosis, thromboembolism, thrombic occlusion and reclusion, restenosis, transient ischemic attack, and first or subsequent thrombotic stroke comprising the subcutaneous administration of a sub-therapeutic dose of a low molecular weight heparin in combination with a sub-therapeutic dose of a platelet GPIIb/IIIa antagonist to a mammal at risk of developing one or more of said conditions.

DETAILED DESCRIPTION OF THE INVENTION

The combinations of a GPIIb/IIIa antagonist with either aspirin or a low molecular weight heparin is useful in the treatment of thrombotic disorders including atherosclerotic arterial disease, valvular heart disease, cerebrovascular disease such as stroke, atrial fibrillation, coronary artery disease such as myocardial infarction and unstable angina, coronary artery bypass grafts, peripheral vascular disease, thromboembolic complications of prosthetic cardiovascular devices such heart valves and vascular grafts. These combinations are also expected to be useful when coupled with endovascular stenting procedures, such as percutaneous transluminal coronary angioplasty, to prevent subsequent arterial thrombus formation and reocclusion. Also useful in the treatment of thrombosis is the combination in a therapeutically effective amount of tissue plasminogen activator and the GPIIb/IIIa antagonist compound (B), described herein.

Aspirin useful in the combination of the present invention is commercially available and well known in the art. Low molecular weight heparins such as dalteparin (fragmin) useful in the combination of the present invention are also commercially available and well known in the art. Preferred GPIIb/IIIa antagonist compounds useful herein, as well as their preparation, are described in WO 95/14683, U.S. Pat. No. 5,849,736 (the contents of which are herein incorporated by reference). Preferred compounds described therein and the preparation thereof have the formula:
Compound (A):

and Compound (B):

other salts and prodrug forms of these compounds are also preferred.

An embodiment of the present invention describes a method for treating a condition selected from the group: acute coronary ischemic syndrome, thrombosis, thromboembolism, thrombic occlusion and reclusion, restenosis, transient ischemic attack, and first or subsequent thrombotic stroke comprising administration of a sub-therapeutic dose of a low molecular weight heparin and a sub-therapeutic dose of a platelet GPIIb/IIIa antagonist to a mammal at risk of developing one or more of said conditions. In a preferred embodiment of the present invention the platelet GPIIb/IIIa antagonist is roxifiban. In a preferred embodiment of the present invention the low molecular weight heparin is tinzaparin. In a preferred embodiment of the present invention the administration is subcutaneous.

Another embodiment of the present invention describes a pharmaceutical composition comprising a platelet GPIIb/IIIa antagonist and a low molecular weight heparin and a pharmaceutically acceptable carrier. In a preferred embodiment of the present invention the platelet GPIIb/IIIa antagonist is roxifiban. In a preferred embodiment of the present invention the low molecular weight heparin is tinzaparin.

Another embodiment of the present invention describes a kit comprising a platelet GPIIb/IIIa antagonist and a low molecular weight heparin for subcutaneous injection.

Another embodiment of the present invention describes a method of treating thrombosis in a mammal comprising administering to said mammal a combination of: (i) a subtherapeutic dose of GPIIb/IIIa antagonist selected from the group consisting of abciximab, eptifibatide, tirofiban, lamifiban, lefradafiban, sibrafiban, orbofiban, xemilofiban, a compound of the formula (A):

and a compound of the formula (B):

and (ii) aspirin or (iii) a low molecular weight heparin selected from the group consisting of tinzaparin, certoparin, parnaparin, nadroparin, ardeparin, enoxaparin, reviparin, reviparin and dalteparin. In a preferred embodiment of the present invention the combination of (i) and (ii) or (iii) provides a synergistic effect. In a preferred embodiment of the present invention the combination administered is a molecular weight heparin. In a preferred embodiment of the present invention the GPIIb/IIIa antagonist is embodiment of the present invention the GPIIb/IIIa antagonist is compound A or compound B. In a preferred embodiment of the present invention the low molecular weight heparin is dalteparin. In a more preferred embodiment of the present invention the GPIIb/IIIa antagonist is compound A or compound B and the low molecular weight heparin is dalteparin.

Another embodiment of the present invention use of a combination of: (i) a subtherapeutic dose of GPIIb/IIIa antagonist selected from the group consisting of abciximab, eptifibatide, tirofiban, lamifiban, lefradafiban, sibrafiban, orbofiban, xemilofiban, a compound of the formula (A):

and a compound of the formula (B):

and (ii) aspirin or (iii) a low molecular weight heparin selected from the group consisting of tinzaparin, certoparin, parnaparin, nadroparin, ardeparin, enoxaparin, reviparin, and dalteparin (fragmin) for the manufacture of a medicament for the treatment of thrombosis.

Another embodiment of the present invention describes a method of treating thrombosis in a mammal comprising administering to said mammal (i) tissue plasminogen activator and (ii) a compound of the formula:

wherein at least one of (i) or (ii) is administered in a subtherapeutic amount.

Specific examples of useful GPIIb/IIIa antagonist compounds are roxifiban, abciximab, eptifibatide, tirofiban, lamifiban, lefradafiban, sibrafiban (Ro-48-3657), orbofiban and xemilofiban described in the paper of Graul et al. and Scarborough (Graul A, Martel A M and Castaner J. Xemilifiban; Drugs of the Future 22: 508–517, 1997; Scarborough R M; Eptifibatide. Drugs of the Future 23: 585–590, 1998). of these, roxifiban, lamifiban, lefradafiban, sibrafiban, orbofiban and xemilofiban are preferred. Others will be readily apparent to those skilled in the art.

Figure 1:
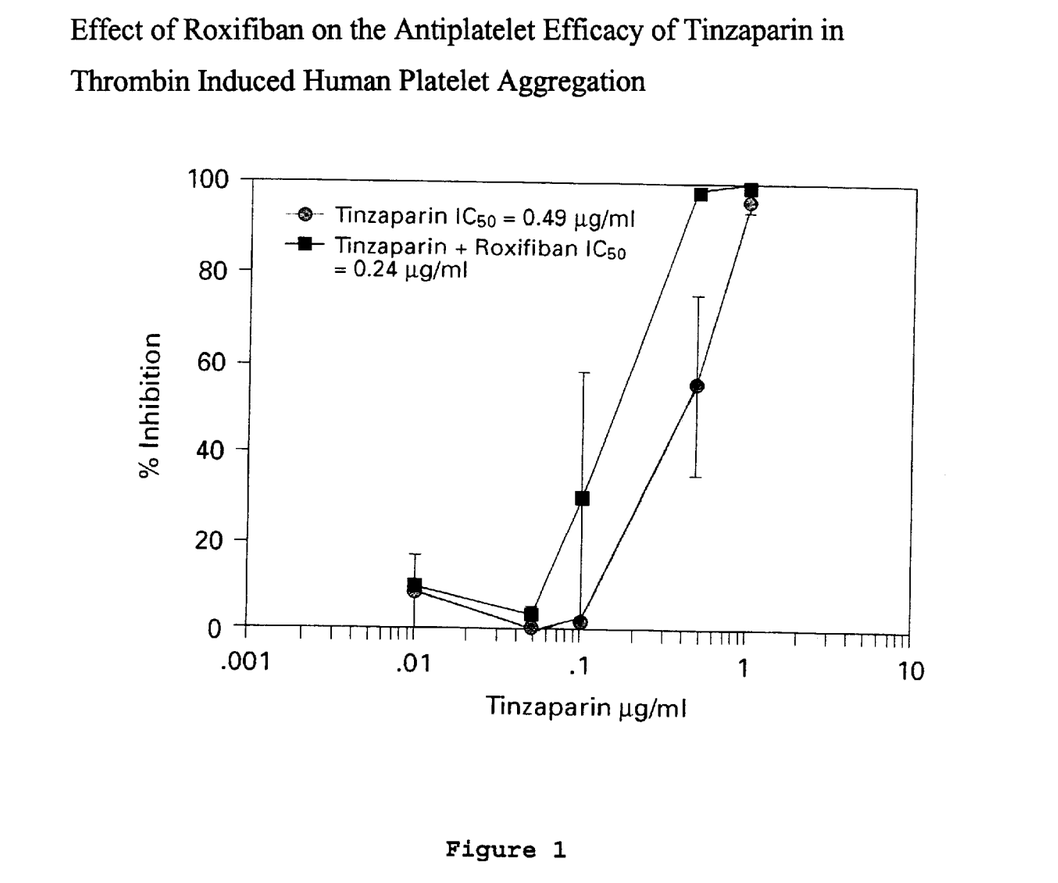
FIG. 1. Graph illustrating the effect of roxifiban on the antiplatelet efficacy of tinzaparin in thrombin-induced human platelet aggregation.
Figure 2:
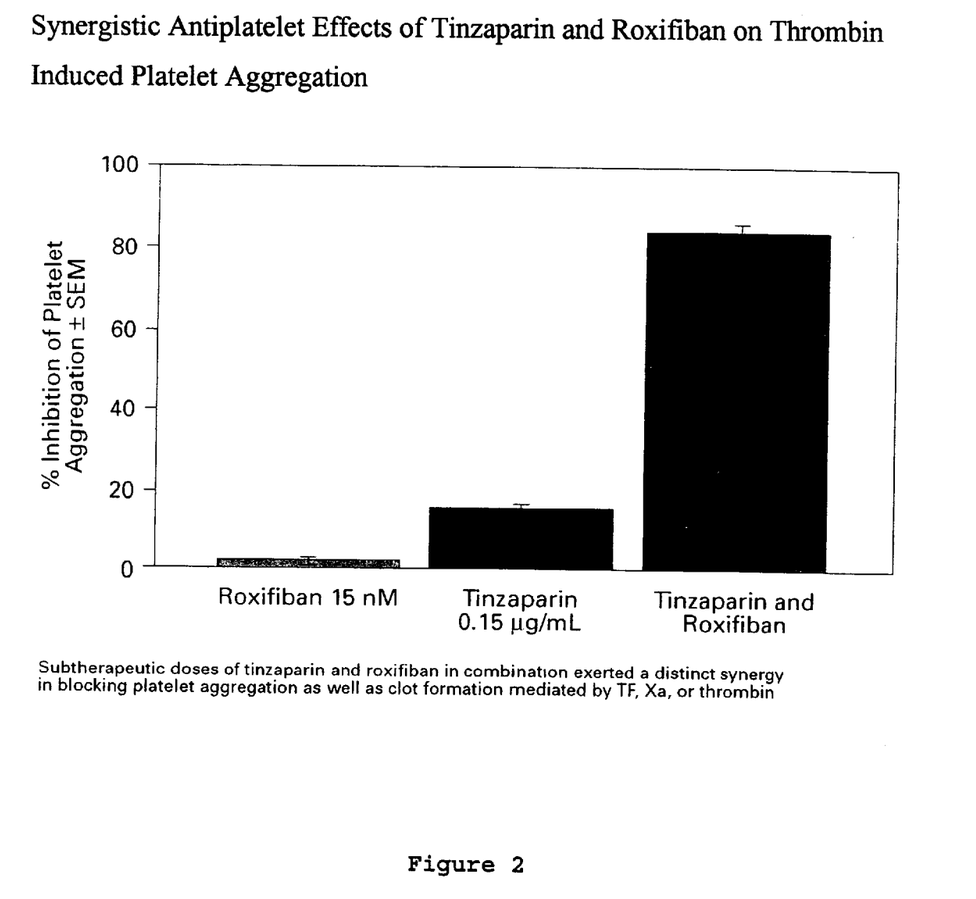
FIG. 2. Graph illustrating the syngeristic antiplatelet effects of tinzaparin and roxifiban on thrombin-induced platelet aggregation.

The effects of the combination of tinzaparin and the platelet GPIIb/IIIa antagonist roxifiban on clot formation and platelet-platelet aggregate formation were studied using thromboelastography (TEG) for platelet-fibrin clot dynamic studies, and light-transmittance aggregometry (LTA) for platelet-platelet interaction studies. The effect of GPIIb/IIIa blockade by roxifiban at sub-therapeutic concentration on the $IC_{50}$ tinzaparin demonstrated a significant, 2-fold shift of the $IC_{50}$. LTA was also utilized to study this interaction. Roxifiban has as a steep dose-response relationship like any other GPIIb/IIIa antagonist. A significant enhancement of tinzaparin's efficacy was shown when roxifiban was combined at sub-therapeutic concentration with different concentrations of tinzaparin (FIG. 1), suggesting a synergistic enhancement of the anti-platelet efficacy of roxifiban by tinzaparin and vice versa (FIG. 2). Combining potent GPIIb/IIIa antagonists such as abciximab with LMWHs results in a similar synergistic interaction. Tissue factor pathway inhibitor (TFPI) can inhibit tissue factor (TF), modulate integrin, down-regulate pro-inflammatory stimuli, provide cytoprotective, anti-platelet effects, modulate Xa, and leukocyte functions. Different LMWHs administered intravenously to non-human primates at equivalent anti-Xa units demonstrated different levels of activity in releasing free TFPI compared to other LMWHs. Additionally, tinzaparin inhibited TF-induced expression of platelet P-selectin, which is important in the modulation of leukocyte-platelet binding and induction of inflammatory stimuli.

The interaction between platelet GPIIb/IIIa receptor antagonists and LMWHs may have tremendous clinical implications. LMWHs may enhance the anti-platelet activity of GPIIb/IIIa antagonists by inhibiting thrombin and Xa. At the same time, GPIIb/IIIa antagonists may potentiate the anti-coagulant action of LMWHs by blocking fibrinogen binding and aggregation regardless of the activating stimulus; they also contribute to the down-regulation of procoagulant activity on the platelet surface. The combination of reduced dose of an LWMH with a reduced dose of a GPIIb/IIIa antagonist may result in a higher therapeutic index.

In treating venous thrombosis and, to a certain extent, acute ischemic syndromes, low-molecular-weight heparin (LMWH) has a more convenient delivery method (subcutaneous) for outpatient use and improved efficacy and safety compared with unfractionated heparin. Computerized Thromboelastography (TEG) was used to determine the ability of platelets and fibrin to augment the shear elastic modules of blood clots. This augmentation was quantified under conditions of maximal platelet activation during clot formation accelerated by recombinant human tissue factor (TF). A comparative efficacy between LMWHs on different mediator-induced clot retraction in human blood using TEG measurements was carried out. These data demonstrated the potency of different LMWHs in inhibiting various mediator-induced clot formations under shear. Tinzaparin demonstrated relatively higher potency in inhibiting TF, lipopolysaccharide (LPS), Xa, and thrombin-induced clot formation under shear. The data suggest a broader efficacy of LMWH compared with other anticoagulant mechanisms. Under these conditions, platelets significantly enhance clot strength eight folds (relative to platelet-free fibrin clots). Abciximab and roxifiban inhibited enhancement of clot strength by affecting the transmission of platelet contractile force to fibrin via platelet GPIIb/IIIa receptors. Tinzaparin demonstrated high potency in inhibiting clot formation, mediated by TF, Xa, or thrombin. The combination of sub-therapeutic tinzaparin and sub-therapeutic roxifiban or Abciximab resulted in distinct synergy in improving anti-platelet and anticoagulant efficacy, mediated by TF, Xa, or thrombin. These data support the usefulness of low-dose tinzaparin with low-dose GPIIb/IIIa antagonists, such as Abciximab or roxifiban, in the prevention and treatment of different thromboembolic disorders.

Compared to unfractionated heparin (UFH), LMWHs exhibit improved subcutaneous (SC) bioavailability; lower protein binding; longer half-life; variable number of antithrombin III binding sites; variable glycosaminoglycan contents; variable anti-serine protease activities (anti-Xa, anti-IIa, and anti-Xa/anti-IIa ratio); variable potency in releasing TPFPI; variable levels of vascular endothelial cell binding kinetics; and hence variable vascular protective effects. For these reasons, over the last decade LMWHs have increasingly replaced UFH in the prevention and treatment of venous thromboembolic disorders (VTE). Randomized clinical trials have demonstrated that individual LMWHs used at optimized dosages are at least as effective and probably safer than UFH. The convenient once- or twice-daily SC dosing regimen without the need for monitoring has encouraged the wide use of LMWHs. It is well established that different LMWHs vary in their physical and chemical properties due to the differences in their methods of manufacturing. These differences translate into differences in their pharmacodynamic and pharmacokinetic characteristics. The World Health Organization (WHO) and United States Food and Drug Administration (FDA) regard LMWHs as individual drugs that cannot be used interchangeably.

As used herein, the phrase "therapeutically effective amount" is intended to include an amount of a combination of compounds claimed effective to treat thrombosis in a mammal. The combination of compounds is preferably a synergistic combination. "Synergy", as described for example by Chou and Talalay, Adv. Enzyme Regul. 22:27–55 (1984), occurs when the effect (in this case, an antithrombotic effect) of the compounds when administered in combination is greater than the additive effect of the compounds when each is administered alone as a single agent. In general, a synergistic effect is most clearly demonstrated at subtherapeutic amounts of one or more of the combined compounds. Synergy can be in terms of antihypertensive effect, antithrombotic effect, or some other non-additive beneficial effect of the combination compared with the individual components.

The terms "administered in combination", "combination", or "combined" when referring to compounds described herein, means the compounds or components are administered concurrently to the mammal being treated. When administered in combination each compound or component or component may be administered at the same time or sequentially in any order or at different points in time, so as to provide the desired therapeutic effect. By "subtherapeutic amount", it is meant that each component when administered to a mammal alone does not give the desired therapeutic effect for the disease being treated.

"Prodrugs", as the term is used herein, are intended to include any covalently bonded carriers which release an active parent drug of the present invention in vivo when such prodrug is administered to a mammalian subject. Since prodrugs are known to enhance numerous desirable qualities of pharmaceuticals (i.e., solubility, bioavailability, manufacturing, etc.) the compounds of the present invention may be delivered in prodrug form. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfydryl group, respectively. Examples of prodrugs include, but are not limited to, acetate, formate, and benzoate derivatives of alcohol and amine functional groups in the compounds of the present invention.

Dosage and Formulation

Combinations of GPIIb/IIIa antagonists and either aspirin or low molecular weight heparin, as well as TPA and the GPIIb/IIIa antagonist compound B, are administered as treatment for thrombosis by any means that produces contact of the agents with their site of action, i.e., the GPIIb/IIIa receptor, in the body of a mammal. They can be administered by any conventional means available for use in conjunction with pharmaceuticals, either as individual therapeutic agents or in a combination of therapeutic agents.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, 19th ed., Mack Publishing Company, Easton, Pa., 1995, a standard reference text in this field, the contents of which are herein incorporated by reference.

Useful pharmaceutical dosage-forms for administration of the compounds of this invention can be illustrated as follows:

Capsules

A large number of unit capsules can be prepared by filling standard two-piece hard gelatin capsules each with 0.1 to 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 0.1 to 100 mg of the active ingredient. The capsules should then be washed and dried.

Tablets

A large number of tablets can be prepared by conventional procedures so that the dosage unit is 0.1 to 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 0.1 to 100 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 0.1 to 100 mg by weight of active ingredient in 10% by volume propylene glycol and water. The solution is sterilized by commonly used techniques.

The combined compounds of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for combined compounds wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of combined compounds in which the one compound is coated with a sustained and/or enteric release polymer, and the other compound is also coated with a polymer such as a low viscosity grade of hydroxypropyl methylcellulose or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric-coated compound and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the combined compounds, whether administered in a single dosage form or administered in separate forms but at the same time or concurrently by the same manner, will be readily apparent to those skilled in the art, based on the present disclosure.

Combination Therapy

Each therapeutic compound of this invention can independently be in any dosage form, such as those described above, and can also be administered in various ways, as described above. For example, the compounds may be formulated together, in a single dosage unit (that is, combined together in one capsule, tablet, powder, or liquid, etc.) as a combination product. Alternatively, when not formulated together in a single dosage unit, an individual GPIIb/IIIa antagonist may be administered at the same time as either aspirin, a low molecular weight heparin or TPA, or sequentially, in any order thereof. When not administered at the same time, preferably the separate administrations of the compounds occur less than about one hour apart.

Preferably, the route of administration of therapeutic combinations herein is by subcutaneous injection. Although it is generally preferred that the compounds are administered by the same route of administration, it is not necessary for this to be so. For example, when a GPIIb/IIIa antagonist and aspirin are administered as a therapeutic combination, it may be preferable for the antagonist to be administered intravenously and aspirin to be administered orally.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of a GPIIb/IIIa antagonist and aspirin combination, a GPIIb/IIIa antagonist and low molecular weight heparin combination, or a TPA compound B combination, is readily ascertainable by a medical practitioner skilled in the art, based upon the present disclosure. By way of general guidance, typically a daily dosage may be about 0.01 milligram to about 1 gram of each component. By way of general guidance, when the compounds are administered in combination, the dosage amount of each component may be reduced by about 70–80% relative to the usual dosage of the component when it is administered alone as a single agent for the treatment of thrombosis, in view of the synergistic effect of the combination.

Obviously, numerous modifications and variations of the present invention are possible in light of the above teachings. It is therefore to be understood that within the scope of the appended claims, the invention may be practiced otherwise than as specifically described herein.

EXAMPLES

The invention can be understood further by the following examples. Other features of the invention will become apparent to those skilled in the art during the following description and exemplary embodiments that are given for illustration and are not intended to be limiting thereof. Saline (0.9 weight % NaCl) is the vehicle in all examples.

Example 1

The Combination of Aspirin and a GPIIb/IIIa Antagonist

Rabbits were anesthetized with ketamine (50 mg/kg i.m.) and xylazine (10 mg/kg i.m.) and then surgically prepared with arterial and venous catheters. An electromagnetic flow probe was placed on a segment of an isolated carotid artery to monitor blood flow. Thrombus formation was induced by electrical stimulation of the carotid artery for 3 min at 4 mA using an external stainless-steel bipolar electrode. Carotid blood flow was measured continuously over a 90-min period to monitor thrombus occlusion. Test agents were infused intravenously 1 hour prior to the electrical stimulation of the carotid artery and continuously during the 90-min period.

Figure 3:
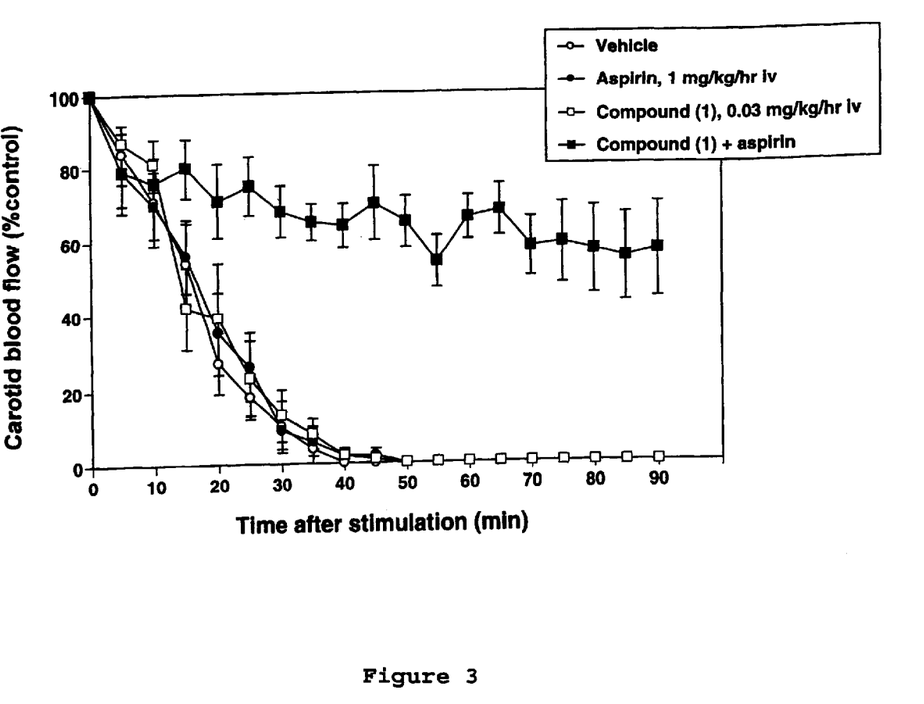
FIG. 3. Graph illustrating carotid blood flow versus time for saline vehicle, aspirin alone, a GPIIb/IIIa antagonist alone, and a combination of aspirin and the same GPIIb/IIIa antagonist.

As shown in FIG. 3, following the electrical stimulation, thrombus formation was induced and carotid blood flow was gradually declined in saline vehicle-treated animals. At about 40 min after stimulation, the artery was totally occluded and blood flow was zero. Aspirin at 1 mg/kg/hr i.v. (concentration in saline was 0.167 mg/ml) or Compound (A) (a GPIIb/IIIa antagonist) at 0.03 mg/kg/hr i.v. (concentration in saline was 0.005 mg/ml) did not prevent the occlusion of the artery; and blood flow in these animals was decreased to zero at about the same time as those in vehicle-treated animals. Surprisingly, Compound (A) 0.03 mg/kg/hr i.v. in combination with aspirin at 1 mg/kg/hr i.v. prevented the artery from occlusion and maintained the blood flow at a level of 60–70% of the control level for greater than 90 min. These results indicate that a combination of Compound (A) and aspirin at their subtherapeutic doses unexpectedly produced a significant antithrombotic effect in a rabbit model of arterial thrombosis.

Example 2

The Combination of Dalteparin (Fragmin) and a GPIIb/IIIa Antagonist

Figure 4:
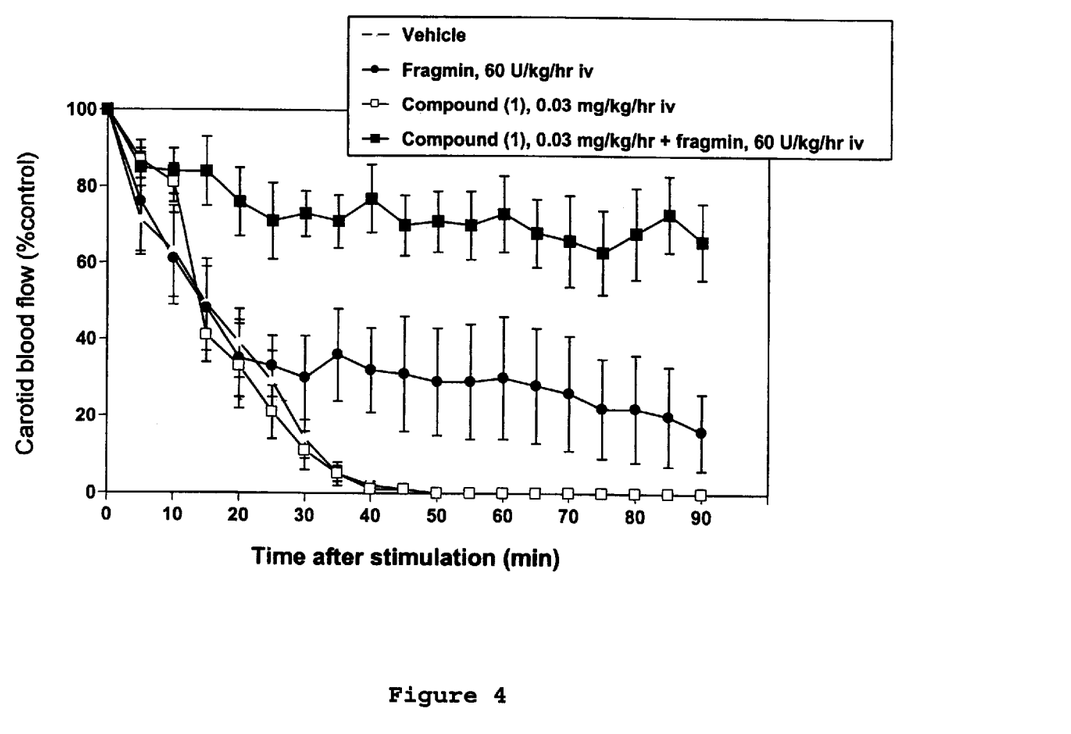
FIG. 4. Graph illustrating carotid blood flow versus time for saline vehicle, dalteparin (fragmin) alone, a GPIIb/IIIa antagonist alone, and a combination of dalteparin and the same GPIIb/IIIa antagonist.

The same experimental protocol as described in Example 1 was used in this study. As shown in FIG. 4, following the electrical stimulation, thrombus formation was induced and carotid blood flow was gradually declined in saline vehicle-treated animals. At about 40 min after stimulation, the artery was totally occluded and blood flow was zero. Fragmin at 60 U/kg/hr i.v. (concentration in saline was 10 U/ml) was not very effective in increasing the blood flow. Compound (A) (a GPIIb/IIIa antagonist ) at 0.03 mg/kg/hr i.v. (concentration in saline was 0.005 mg/ml) was not effective and blood flow in these animals was decreased to zero at about the same time as those in saline vehicle-treated animals. Surprisingly, Compound (A) at 0.03 mg/kg/hr i.v. in combination with dalteparin (fragmin) at 60 U/kg/hr i.v. prevented the artery from occlusion and maintained the blood flow at a level of 60–70% of the control level for greater than 90 min. These results indicate that a combination of Compound (A) and dalteparin (fragmin) at their subtherapeutic doses unexpectedly produced a significant antithrombotic effect in a rabbit model of arterial thrombosis.

Example 3

The Combination of Tissue Plasminogen Activator and a GPIIb/IIIa Antagonist

Experiments were conducted in rats anesthetized with ketamine (110 mg/kg i.m.) and xylazine (10 mg/kg i.m.). The protocol is similar to the rabbit protocol as described above in Example 1 except that the free acid of a compound of the formula (B):

or the free acid of sibrafiban and/or TPA were given 5 min after a preformed clot was formed. The measured parameters were time to reperfusion, duration of patency and incidence of reocclusion. The doses of TPA, sibrafiban and compound B used were 1, 0.3 and 0.3 mg/kg i.v., respectively. The doses of sibrafiban and compound B used in this study were equal effective in preventing thrombosis in this rat model.

As shown in Table 1 below, a combination of compound B and TPA produced unexpectedly better thrombolytic effect than the combination of sibrafiban and TPA. This result suggests that compound B is a promising useful adjunctive agent, which accelerates thrombolysis induced by TPA or other thrombolytic agents. In addition, this result also shows that compound B exerted a better enhancement of the thrombolysis induced by a subtherapeutic dose of TPA than sibrafiban.

TABLE 1

|  | TPA (n = 17) | Sibrafiban + TPA (n = 14) | Compound B + TPA (n = 14) |
| --- | --- | --- | --- |
| Time to reperfusion (min) | 32 ± 6 | 30 ± 4 | 16 ± 2* |
| Duration of patency (%) | 29 ± 2 | 63 ± 6* | 84 ± 2*, ** |
| Incidence of reocclusion | 15/17 | 6/14* | 1/14*, ** |

*P < .05, compared to TPA
**P < .05, compared to sibrafiban + TPA

Example 4

Figure 5:
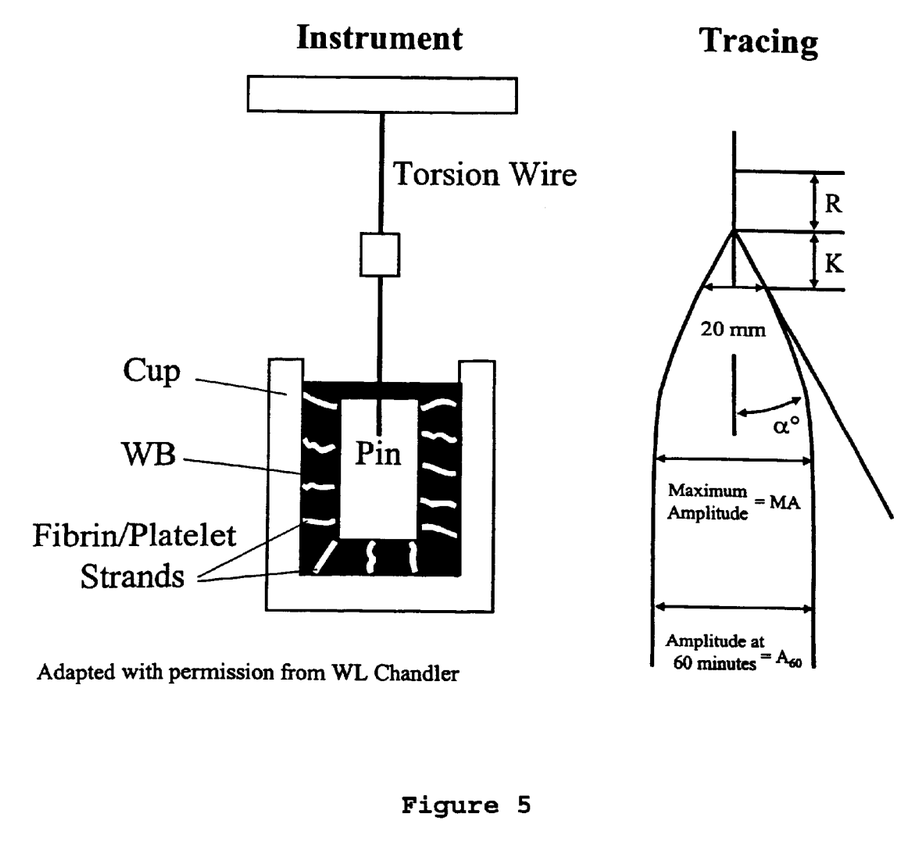
FIG. 5. Schematic illustration of the instrumentation utilized in thromboelastography and the parameters of the measurements.

Computerized Thromboelastography (FIG. 5)

Clot formation was monitored at 37° C. in an oscillating plastic cylindrical cuvette ("cup") and a coaxially suspended stationary piston ("pin") with a 1 mm clearance between the surfaces, using a computerized Thrombelastograph (CTEG Model 3000, Haemoscope, Skokie, IL). The cup oscillates 4°45' (1/12 radian) in either direction every 4.5 seconds, with a 1 second mid-cycle stationary period; resulting in a frequency of 0.1 Hz and a maximal shear rate of 0.1 per second. The pin is suspended by a torsion wire that acts as a torque transducer. With clot formation, fibrin fibrils physically link the cup to the pin and the rotation of the cup (Transmitted to the pin) is displayed on-line using an IBM-compatible personal computer and customized software (Haemoscope Corp., Skokie, Ill.). The torque experienced by the pin (relative to the cup's oscillation) is plotted as a function of time. The amplitude on the TEG tracing is a measure of the rigidity of the clot; the peak strength or the shear elastic modulus attained by the clot, G, is a function of clot rigidity and can be calculated from the maximal amplitude (MA) of the TEG tracing.

The following parameters were measured from the TEG tracing (FIG. 5):

R, the reaction time (gelation time) represents the latent period before the establishment of a 3-dimensional fibrin gel network (with measurable rigidity of amplitude=2 mm).

Maximum Amplitude (MA, in mm) is the peak rigidity manifested by the clot.

Shear elastic modulus or clot strength (G, dynes/cm$^2$) is defined by: G=(5000* MA)/(96-MA) for computerized TEG.

Blood Sampling: Blood was drawn from consenting volunteers under a protocol approved by the Human Investigations Committee of William Beaumont Hospital. Using the two-syringe method, samples were drawn through a 21 gauge butterfly needle and the initial 3 ml blood was discarded. Whole blood (WB) was collected into siliconized Vacutainer tubes (Becton Dickinson, Rutherford, NJ containing 3.8% trisodium citrate such that a ratio of citrate whole blood of 1:9 (v/v) was maintained. TEG was performed within 3 hrs of blood collection.

Example 5

Platelet Contribution to Clot Strength

To assess the effect of the TF modification on peak clot strength (G) was measured with and without the addition of TF in paired samples of WB and PRP. To document the contribution of activated platelets to the elastic modulus of fibrin clots, the effect of platelet number was measured by serially diluting PRP with PPP. The platelet count of each dilution was measured before performing TEG. Tissue factor-triggered TEG was performed with increasing concentrations (0, 0.625, 1.25, 2.5, 5 and 10 $\mu$M) along with DMSO added to the TEG cups such that the final DMSO concentration in each TEG sample was 0.3% (v/v). The effect of GPIIb/IIIa blockade on clot strength was studied by adding increasing concentrations of c7E3 Fab (Abciximab, Centocor, Malvern, Pa.), cyclic peptide, peptidomimetic and non-peptide GPIIb/IIIa antagonists (DuPont, Wilmington, Del.) and various LMWH to the TEG cup along with $CaCl_2$ and TF. The Thrombelastograph maximum amplitude (MA) for platelets MA (PLT)) was calculated by subtracting the MA from a platelet-poor plasma (PPP) sample MA (PPP) determined in one thromboelastography well from that of whole blood MA (WB) run simultaneously in the second thromboelastography well.

Example 6

Platelet Aggregation

Agonist-induced platelet aggregation was measured as change in % light transmission of PRP (platelet count 2×105 per $\mu$L). For studying the effect of LMWH & GPIIb/IIIa antagonists on platelet aggregation, increasing concentrations were added to PRP for 5 minutes after which 0.5 IU/ml thrombin was added. The aggregation response was measured as the maximum response of the increase in light transmission induced by thrombin, using PPP to establish 100% light transmission.

Example 7

Comparative Efficacy Among Different LMWHs in Inhibiting Clot Formation Induced by Different Stimuli in Human Whole Blood Using Thromboelastography

TABLE 2

Mediators of Clot Retraction
Mean ($IC_{50}$ [$\mu$g/mL]) ± SEM

| LMWH | TF 2.5 ng | LPS 6.25 $\mu$g | Xa 0.25 nM | Thrombin 0.3 mU |
|---|---|---|---|---|
| Enoxaparin | 0.95 ± 0.39 | 2.86 ± 0.35 | 0.52 ± 0.15 | 1.19 ± 0.13 |
| Tinzaparin | 0.49 ± 0.06* | 0.94 ± 0.28* | 0.15 ± 0.05* | 0.33 ± 0.02* |
| Fraxiparin | 2.85 ± 0.83 | 3.32 ± 0.85 | 0.98 ± 0.45 | 0.78 ± 0.21 |
| TFPI | ND | 0.09 ± 0.01 | ND | — |

Data represent mean + SEMn = 3.4, — = inactive; ND = no data
*p < 0.01 as compared to enoxaparin or fraxiparin Comparative efficacy among different LMWHs in inhibiting clot formation induced by different stimuli in human whole blood using Thromboelastography: Syngeristic effects of GPIIb/IIIa antagonists:

TABLE 3

| LMWH | Thrombin $IC_{50}$ ($\mu$g/mL) | Thrombin + roxifiban $IC_{50}$ ($\mu$g/mL) |
|---|---|---|
| enoxaparin | 1.19 ± 0.13 | 0.72 ± 0.18 |
| tinzaparin | 0.33 ± 0.03 | 0.15 ± 0.10 |
| fraxiparin | 0.57 ± 0.11 | 0.34 ± 0.08 |
| dalteparin | 0.52 ± 0.16 | 0.24 ± 0.09 |

TABLE 4

Synergy between LMWH and GPIIb/IIIa antagonist roxifiban on thrombin-induced clot retraction in human blood using thromboelastography:

| | Thrombin $IC_{50}$ ($\mu$g/mL) | Thrombin + tinzaparin (0.1 $\mu$g/mL) $IC_{50}$ ($\mu$g/mL) | Thrombin + enoxaparin (0.5 $\mu$g/mL) $IC_{50}$ ($\mu$g/mL) |
|---|---|---|---|
| roxifiban | 110 ± 20 | 61 ± 6.1 | 50 ± 0.5 |

What is claimed is:

1. A method for treating a condition selected from the group: acute coronary ischemic syndrome, thrombosis, thromboembolism, thrombic occlusion and reclusion, restenosis, transient ischemic attack, and first or subsequent thrombotic stroke comprising administration of a sub-therapeutic dose of a low molecular weight heparin and a sub-therapeutic dose of a platelet GPIIb/IIIa antagonist to a mammal in need of such treatment.

2. A method according to claim 1, wherein the platelet GPIIb/IIIa antagonist is roxifiban.

3. A method according to claim 1, wherein the low molecular weight heparin is tinzaparin.

4. A method according to claim 1, wherein the administration is subcutaneous.

5. A pharmaceutical composition comprising a platelet GPIIb/IIIa antagonist and a low molecular weight heparin and a pharmaceutically acceptable carrier.

6. A pharmaceutical composition according to claim 5, wherein the platelet GPIIb/IIIa antagonist is roxifiban.

7. A pharmaceutical composition according to claim 5, wherein the low molecular weight heparin is tinzaparin.

8. A kit comprising a platelet GPIIb/IIIa antagonist and a low molecular weight heparin for subcutaneous injection.

9. A method of treating thrombosis in a mammal comprising administering to said mammal a combination of: (i) a subtherapeutic dose of GPIIb/IIIa antagonist selected from the group consisting of abciximab, eptifibatide, tirofiban, lamifiban, lefradafiban, sibrafiban, orbofiban, xemilofiban, a compound of the formula (A):

and a compound of the formula (B):

and (ii) aspirin or (iii) a low molecular weight heparin selected from the group consisting of tinzaparin, certoparin, parnaparin, nadroparin, ardeparin, enoxaparin, reviparin, reviparin and dalteparin.

10. The method of claim 9 wherein the combination of (i) and (ii) or (iii) provides a synergistic effect.

11. The method of claim 9, wherein the combination administered is a combination of the GPIIb/IIIa antagonist and a low molecular weight heparin.

12. The method of claim 11, wherein the GPIIb/IIIa antagonist is administered in a subtherapeutic amount.

13. The method of claim 11, wherein the GPIIb/IIIa antagonist is compound A or compound B.

14. The method of claim 11, wherein the low molecular weight heparin is dalteparin (fragmin).

15. The method of claim 11, wherein the GPIIb/IIIa antagonist is compound A or compound B and the low molecular weight heparin is dalteparin (fragmin).

16. A method of treating thrombosis in a mammal comprising administering to said mammal (i) tissue plasminogen activator and (ii) a compound of the formula:

* * * * *